United States Patent
Houston et al.

(10) Patent No.: US 7,185,677 B2
(45) Date of Patent: Mar. 6, 2007

(54) HELICAL FORMATION FOR A CONDUIT

(75) Inventors: John Graeme Houston, Perth (GB); Robert Gordon Hood, Longforgan (GB); John Bruce Cameron Dick, Coupar Angus (GB); Craig McLeod Duff, Dundee (GB); Allana Johnstone, Dunblane (GB); Christophe Emmanuel Sarran, Perth (GB); Peter Arno Stonebridge, Perth (GB)

(73) Assignee: Tayside Flow Technologies Limited, Dundee (GB)

( * ) Notice: Subject to any disclaimer, the term of this patent is extended or adjusted under 35 U.S.C. 154(b) by 0 days.

(21) Appl. No.: 10/496,212

(22) PCT Filed: Nov. 21, 2002

(86) PCT No.: PCT/GB02/05242

§ 371 (c)(1),
(2), (4) Date: Oct. 29, 2004

(87) PCT Pub. No.: WO03/045279

PCT Pub. Date: Jun. 5, 2003

(65) Prior Publication Data

US 2005/0061380 A1    Mar. 24, 2005

(30) Foreign Application Priority Data

Nov. 21, 2001  (GB)  ................... 0127888.6

(51) Int. Cl.
*F15D 1/02*    (2006.01)
*A61F 2/06*   (2006.01)

(52) U.S. Cl. .................. 138/39; 138/112; 138/129; 623/1.22; 623/1.32; 623/1.33

(58) Field of Classification Search ................ 138/39, 138/112, 129; 623/1.22, 1.32, 1.33
See application file for complete search history.

(56) References Cited

U.S. PATENT DOCUMENTS

| 2,831,662 | A | * | 4/1958 | Hirsch ........................ 165/156 |
| 4,161,966 | A | * | 7/1979 | Scheffler et al. ............ 138/112 |
| 4,420,019 | A | * | 12/1983 | Dillon ........................ 138/129 |
| 4,553,545 | A | * | 11/1985 | Maass et al. ............... 606/198 |
| 4,760,849 | A | * | 8/1988 | Kropf .......................... 606/191 |
| 5,416,270 | A | * | 5/1995 | Kanao .......................... 174/47 |
| 5,500,013 | A | * | 3/1996 | Buscemi et al. ........... 623/1.22 |
| 5,669,420 | A | * | 9/1997 | Herrero et al. ............. 138/135 |
| 5,924,456 | A |   | 7/1999 | Simon |
| 6,019,779 | A | * | 2/2000 | Thorud et al. .............. 606/198 |
| 6,063,111 | A | * | 5/2000 | Hieshima et al. .......... 623/1.22 |
| 6,156,062 | A | * | 12/2000 | McGuinness .............. 623/1.22 |

(Continued)

FOREIGN PATENT DOCUMENTS

EP    0 077 130    4/1983

(Continued)

*Primary Examiner*—James Hook
(74) *Attorney, Agent, or Firm*—Bracewell & Giuliani LLP

(57) ABSTRACT

A helical formation (2) for a conduit (1). The helical formation (2) comprises an elongate member defining at least a portion of a helix, the elongate member comprising two inwardly extending portions (6, 7). The inwardly extending portions (6, 7) are spaced from each other and extend along the length of the elongate member in side-by-side relationship.

13 Claims, 10 Drawing Sheets

U.S. PATENT DOCUMENTS

| | | | |
|---|---|---|---|
| 6,572,648 B1 * | 6/2003 | Klumb et al. | 623/1.15 |
| 6,645,237 B2 * | 11/2003 | Klumb et al. | 623/1.11 |
| 6,660,032 B2 * | 12/2003 | Klumb et al. | 623/1.13 |
| 6,675,901 B2 * | 1/2004 | Johnson et al. | 166/380 |
| 6,776,194 B2 * | 8/2004 | Houston et al. | 138/39 |
| 6,921,414 B2 * | 7/2005 | Klumb et al. | 623/1.15 |
| 2001/0027693 A1 * | 10/2001 | Blaurock | 74/424.75 |
| 2002/0179166 A1 * | 12/2002 | Houston et al. | 138/39 |
| 2004/0037986 A1 * | 2/2004 | Houston et al. | 428/36.9 |
| 2006/0124187 A1 * | 6/2006 | Houston et al. | 138/39 |

FOREIGN PATENT DOCUMENTS

| | | |
|---|---|---|
| FR | 2 655 548 | 6/1991 |
| WO | WO 00 38591 | 7/2000 |

* cited by examiner

HELICAL FORMATION FOR A CONDUIT

RELATED APPLICATIONS

This application claims the benefit of PCT Patent Application Ser. No. PCT/GB02/05242, filed Nov. 21, 2002 claiming priority to GB 0127888.6 filed on Nov. 21, 2001, titled "A Helical Formation for a Conduit," which is incorporated by reference in its entirety.

The invention relates to a helical formation for a conduit.

A number of documents have proposed using helical formations in conduits to encourage a desired flow pattern of a fluid within the conduit. Such helical formations have been proposed for a wide variety of applications, including pipelines and blood flow tubing. The purpose of the helical formations is generally to generate spiral flow of the fluid within the conduit to reduce turbulence and dead spots within the conduit.

Although the use of helical formations has been proposed as beneficial to fluid flow in conduits by helping to generate spiral fluid flow patterns, there is little or no information on the physical characteristics of the helical formation that is required to create a suitable spiral flow pattern. Clearly, some designs of helical formations will be ineffective at creating spiral flow and others will not create a beneficial spiral flow. For example, helical formations having a high helix angle may tend to create turbulence rather than spiral flow due.

In accordance with a first aspect of the present invention, there is provided a helical formation for a conduit, the helical formation comprising an elongate member defining at least a portion of a helix, the elongate member comprising two inwardly extending portions, the inwardly extending portions being spaced from each other, extending along the length of the elongate member in side-by-side relationship.

The terms "helical", "helix" and "spiral" as used herein cover the mathematical definition of helical and any combination of the mathematical definitions of helical and spiral.

Typically, the longitudinally extending member further comprises an intermediate portion that separates the two Inwardly extending portions.

Preferably, the inwardly extending portions extend inwardly of the helix defined by the longitudinally extending member by substantially the same distance. However, it is possible that they could extend inwardly by different distances.

The helical formation may be in the form of an insert adapted to be inserted into the conduit, in use. The insert may be removably inserted or may be permanently inserted.

Alternatively, the helical formation may be an integral part of a side wall of the conduit. For example, the helical formation may be formed by a deformation of a portion of the side wall of the conduit.

In one example of the invention, the helical formation may be for use in blood flow tubing for the human or animal body. The tubing may be synthetic or natural blood flow tubing. For example, the tubing may be a graft. In another example, the conduit may be a stent for insertion into blood flow tubing in the human or animal body.

An example of a helical formation in accordance with the invention will now be described with reference to the accompanying drawings, in which.

Figure 1:
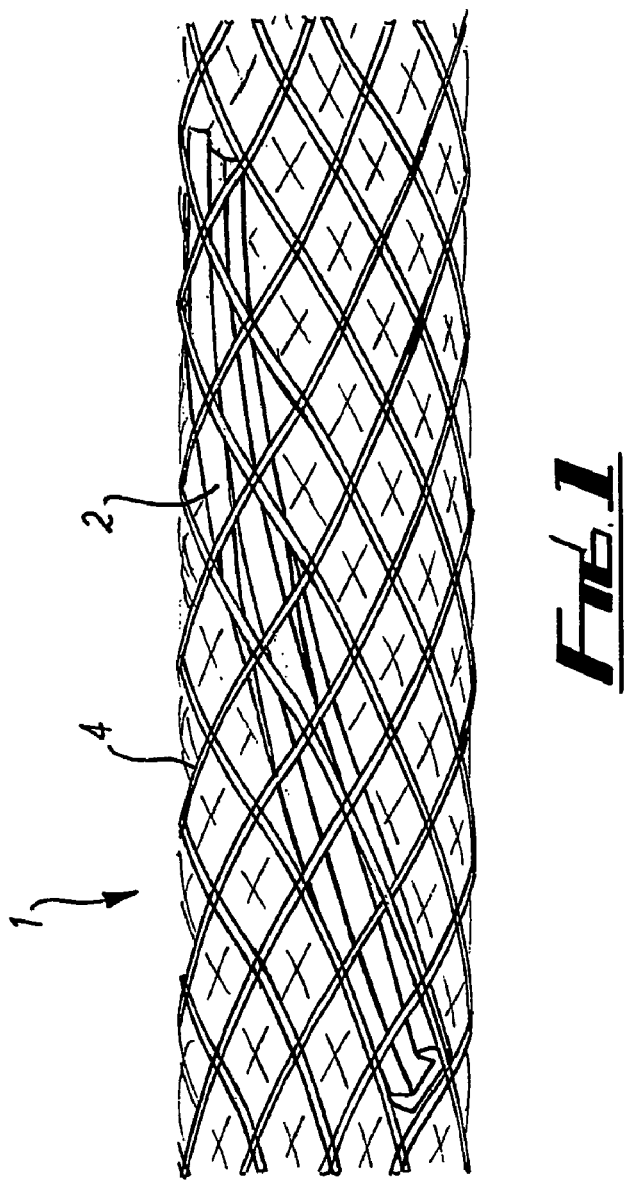
FIG. 1 is a side view of a stent having a helical formation with two fins.
Figure 2:
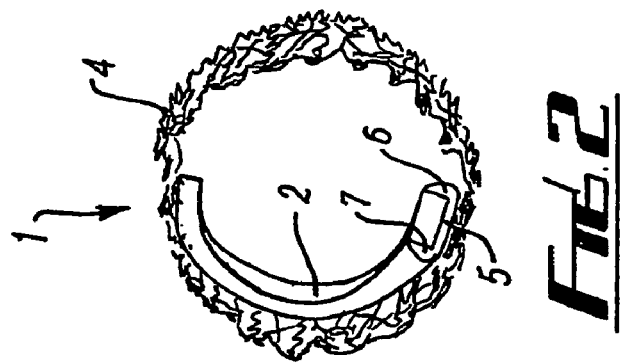
FIG. 2 is an end view of the stent.

FIGS. 1 and 2 show a stent 1 having a main body 4 which is formed from a wire mesh material. Attached to the internal side wall of the body 4 is an insert 2 which defines a portion of a helix. The insert 2 is typically manufactured from a biocompatible material, such as polyurethane, and may be attached to the internal side wall of the body 4 by glue, by injection moulding or by melting base portion 5 of the insert 2 onto the body 4 such that after cooling, the mesh structure of the body 4 is entrained with the base portion 5 of the insert 2.

Figure 3:
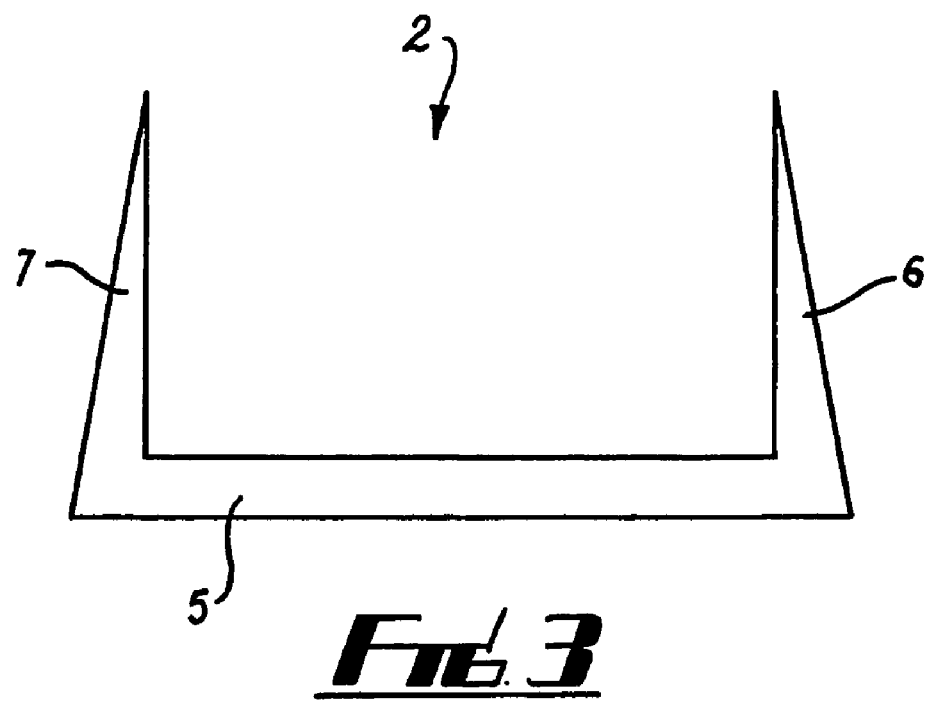
FIG. 3 is a cross-sectional view of the helical formation.

A cross-sectional view of the insert 2 is shown in FIG. 3 where it can be seen that insert 2 also includes two fins 6, 7 extending from the base portion 5 at opposite edges of the base portion 5. It will be noted from FIGS. 1 and 2 that the fins 6, 7 extend along the length of the insert 2 and extend inwardly from the internal side walls of the main body 4.

In use, the stent 1 is inserted into a blood vessel in the human or animal body in a collapsed configuration and after it is located in the correct position, It is expanded to engage with the side walls of the blood vessel to locate the stent 1 in the desired position. Typically, the stent 1 is inserted on a balloon catheter with the stent 1 in the collapsed configuration around the collapsed balloon of the catheter. When the stent 1 is in the correct position in a blood vessel, the balloon is then inflated by pumping fluid into the balloon through the catheter. The expansion of the balloon expands the stent 1 Into engagement with the internal side walls of the blood vessel. The configuration of the stent 1 shown In FIG. 1 is In the expanded position. That is, the configuration after it is engaged with the internal side walls of the vessels by expanding the balloon of a balloon catheter, and the balloon catheter is removed.

Figure 4:
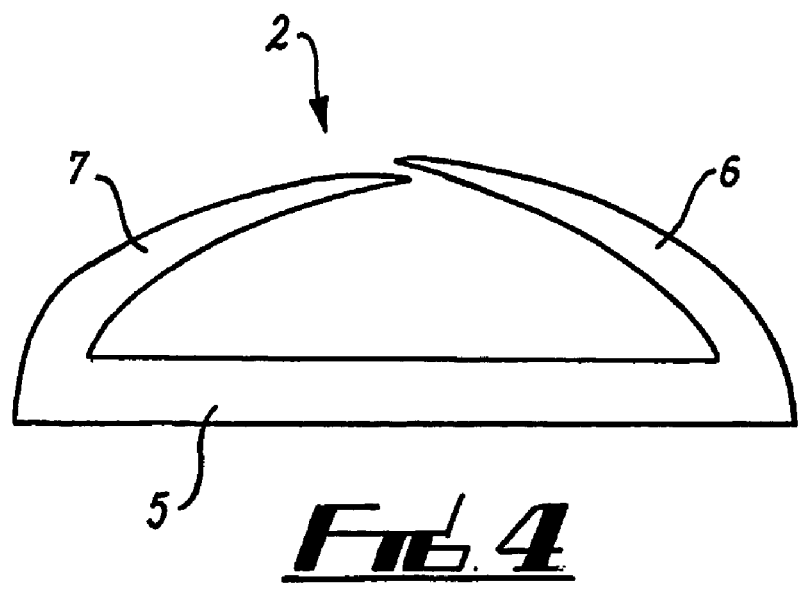
FIG. 4 is a cross-sectional view of the helical formation in a collapsed position.

When the stent 1 is collapsed onto the balloon of the catheter, the insert 2 is designed such that the fins 6, 7 are bent inwardly so that the fins of the insert collapse so as to reduce the volume occupied by the insert 2 when the stent 1 is in the collapsed configuration. This is illustrated in FIG. 4 where it can be seen that fin 7 bends inwardly to overlie the base 5 and fin 6 bends inwardly to overlie the fin 7. This feature is enabled by appropriate design of the base portion 5 and fins 6, 7 and a suitable choice of material for the insert 2. Typically, this is an elastically deformable material, such as a suitable plastic material, for example, polyurethane. Hence, as the collapsing is an elastic deformation of the insert 2, the fins 6, 7 automatically return to the non-collapsed position, shown in FIG. 2, after expansion of the stent 1 and removal of the balloon catheter.

After insertion and placement in the desired blood vessel, the insert 2, due to its helical shape, acts on blood flowing through the stent 1 to generate a spiral flow component in the blood.

The length of the stent 1 is to a large extent dictated by enabling sufficient flexibility to ensure that the stent 1 can be inserted into the desired location in the human or animal body. This is normally performed by insertion through the femoral artery. Accordingly, the stent 1 typically has a length in the region of 10 mm to 70 mm and normally approximately 30 mm to 40 mm in length. In order for the insert 2 to generate spiral flow of blood passing through the stent 1, the helix angle of the helix defined by the insert 2 must not be too high. Therefore, to generate an effective spiral flow component, the insert 2 typically defines only a portion of one revolution of the helix that it defines. Preferably, this is at least 50% of one revolution and most preferably greater than 70% of one revolution, but less than one full revolution.

When blood flows through the stent 1, the helical formation of the insert 2 will tend to generate a spiral flow formation in the blood exiting from the stent 1. This spiral flow tends to reduce turbulence and promote better flow of blood within the blood vessels of the human or animal body into which it is inserted.

Figure 5:
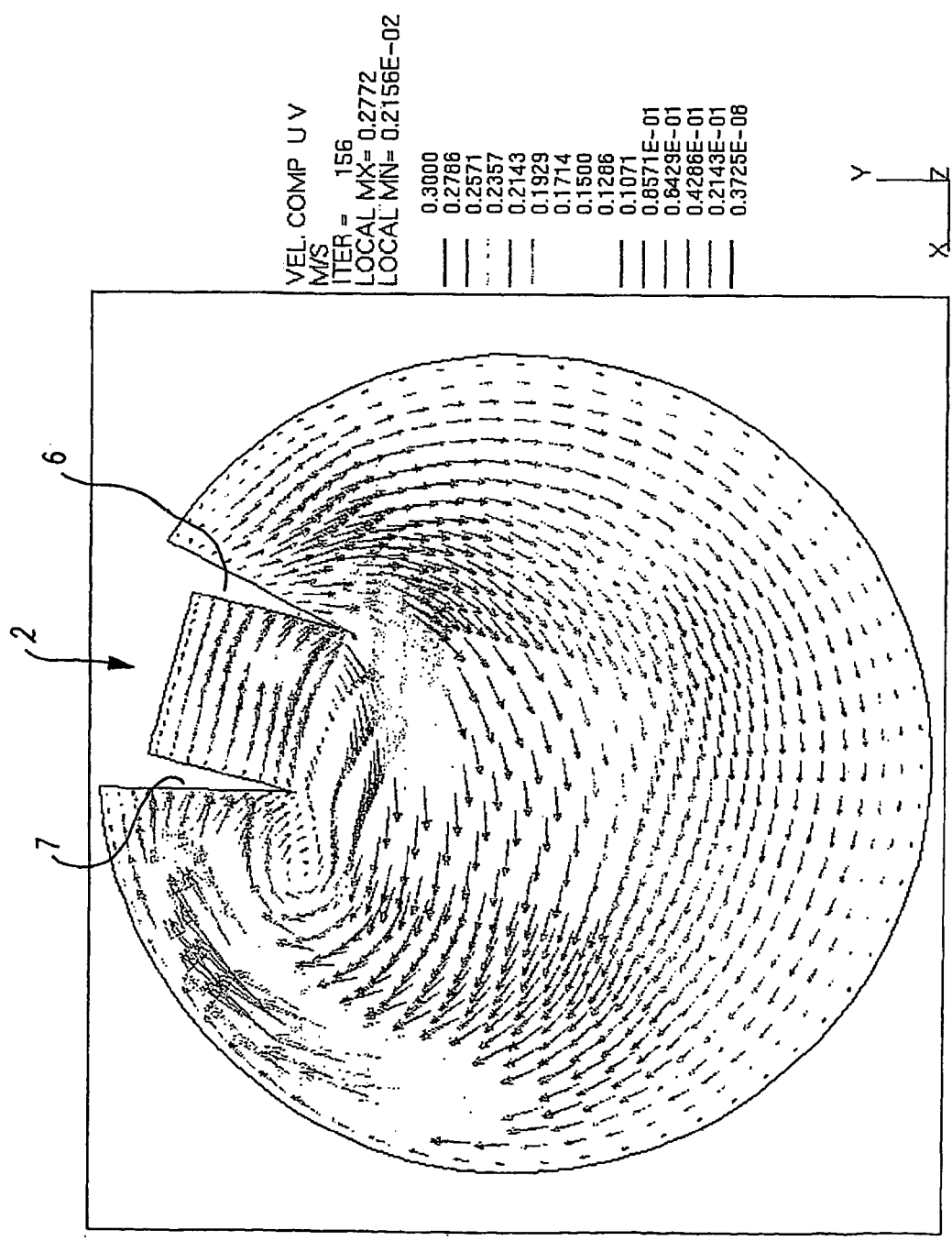
FIG. 5 shows a distribution of flow velocities across the stent 15 mm from the stent inlet.
Figure 6:
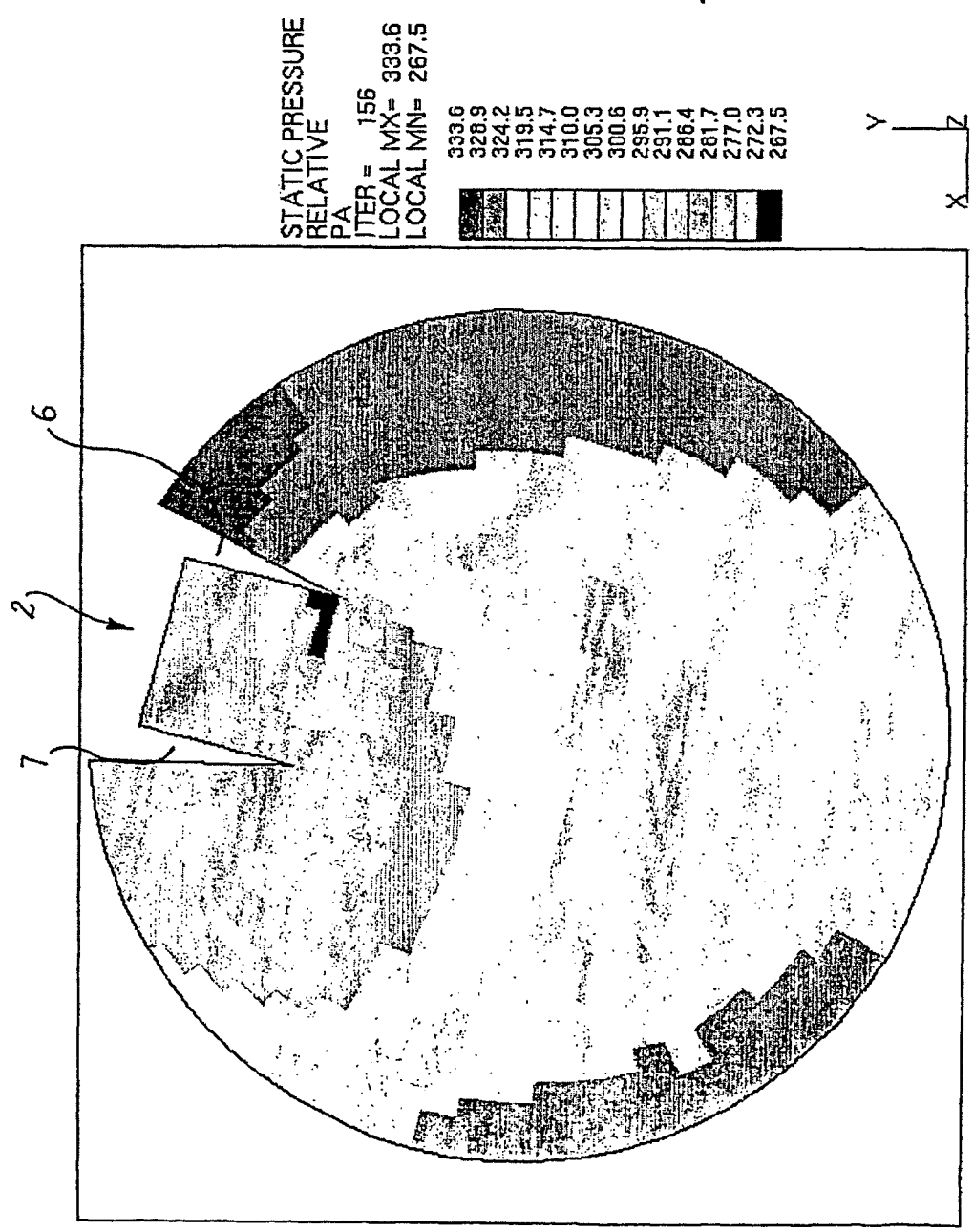
FIG. 6 shows a distribution of fluid pressures across the stent 15 mm from the stent inlet.
Figure 7:
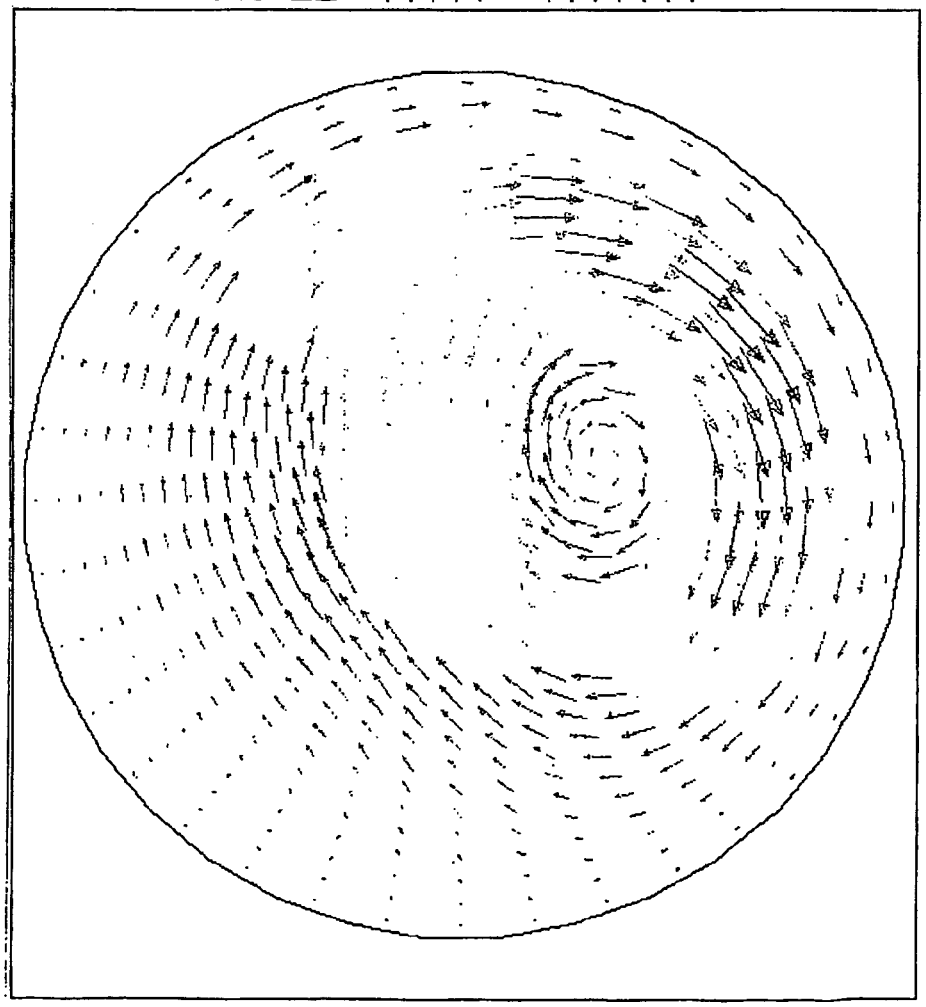
FIG. 7 shows a distribution of flow velocities across the stent 50 mm downstream from the stent exit.
Figure 8:
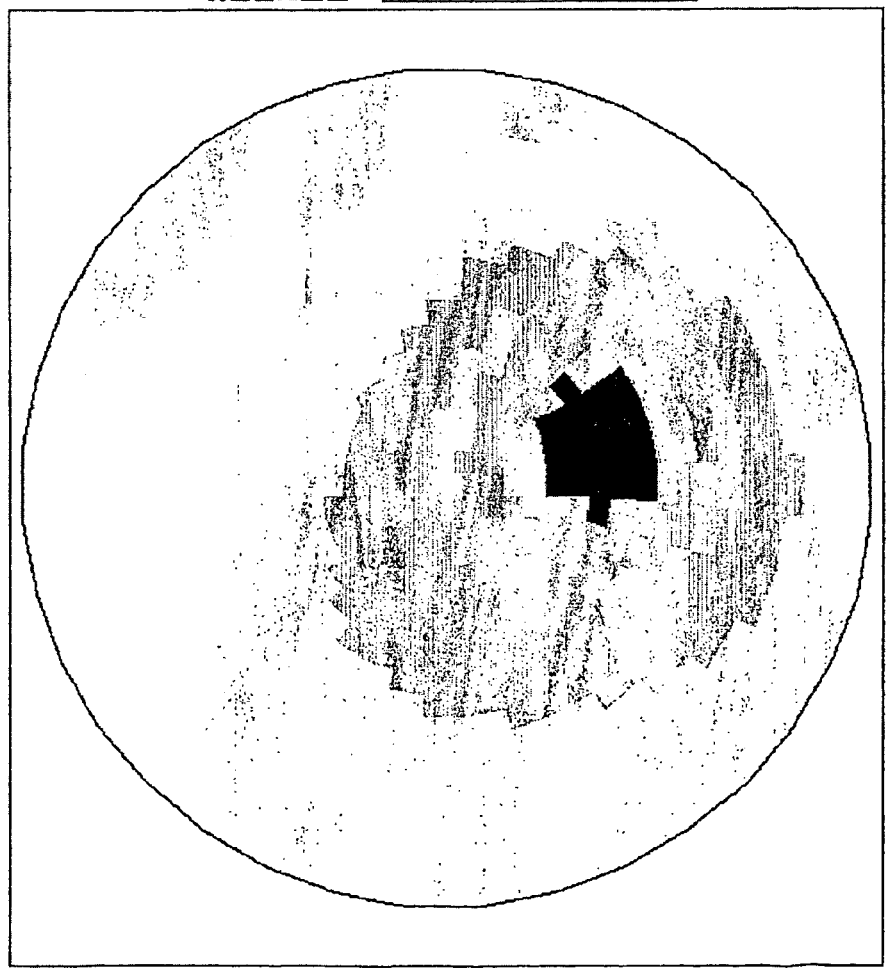
FIG. 8 shows a distribution of fluid pressures across the stent 50 mm downstream from the stent exit.

FIGS. 5 and 6 show the distribution of flow velocities and static pressures, respectively, 15 mm from the inlet of the stent 1 and where the angle of the helix defined by the helical formation 2 is 20° and the stent 1 has a nominal length of 30 mm and a nominal diameter of 8 mm. FIGS. 7 and 8 show the distribution of flow velocities and static pressures, respectively, 50 mm downstream from the outlet of the stent 1. FIGS. 5 and 7 show that the helical formation 2 generates spiral flow with the distribution of flow velocities across the stent I and across the tubing downstream of the stent being relatively uniform and with relatively low turbulence and dead spots. FIGS. 6 and 8 show that the helical formation 2 does not generate unduly high static pressures on the side walls of the stent 1.

Figure 9:
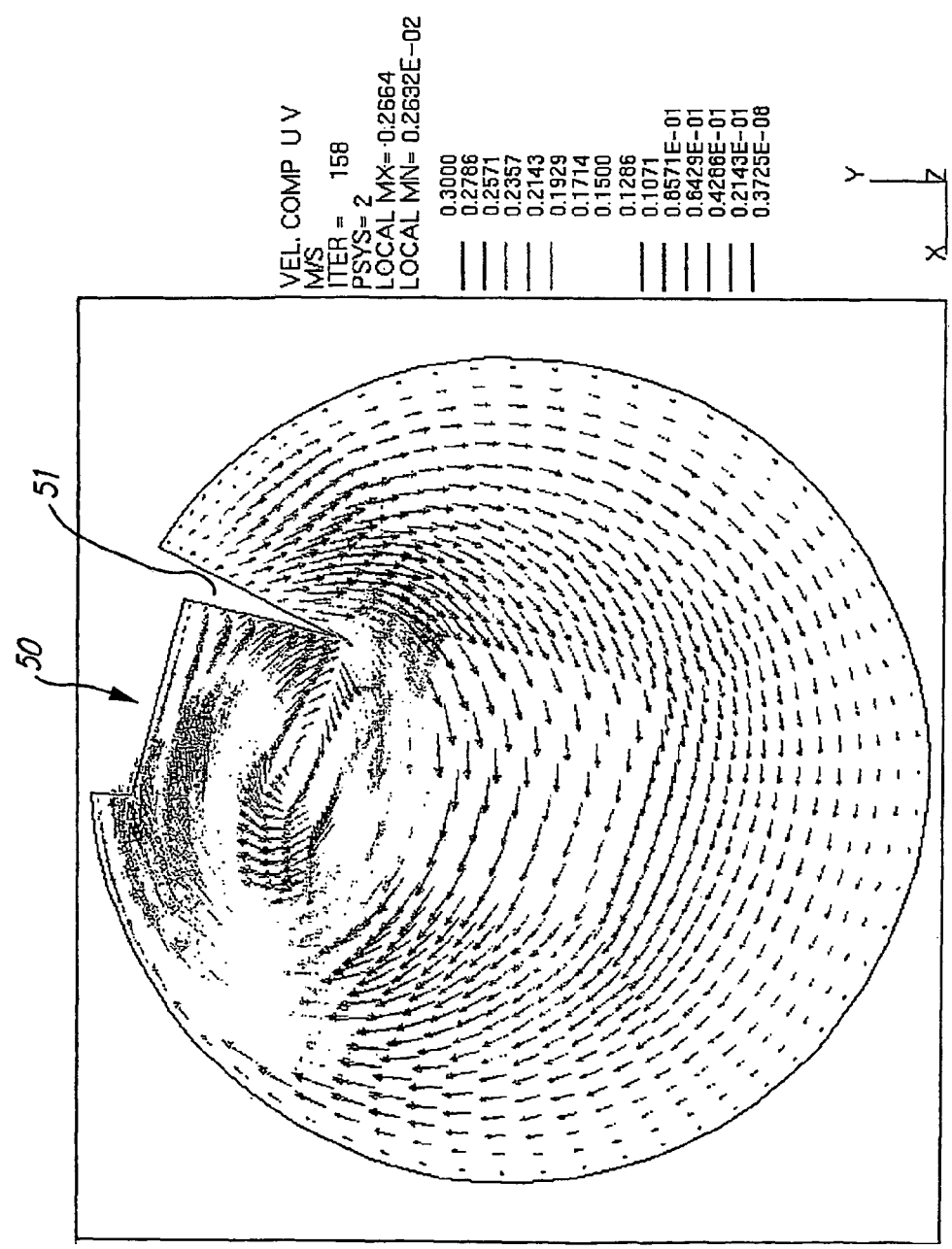
FIG. 9 shows a distribution of flow velocities across a stent having a helical formation with one fin 15 mm from the stent inlet.
Figure 10:
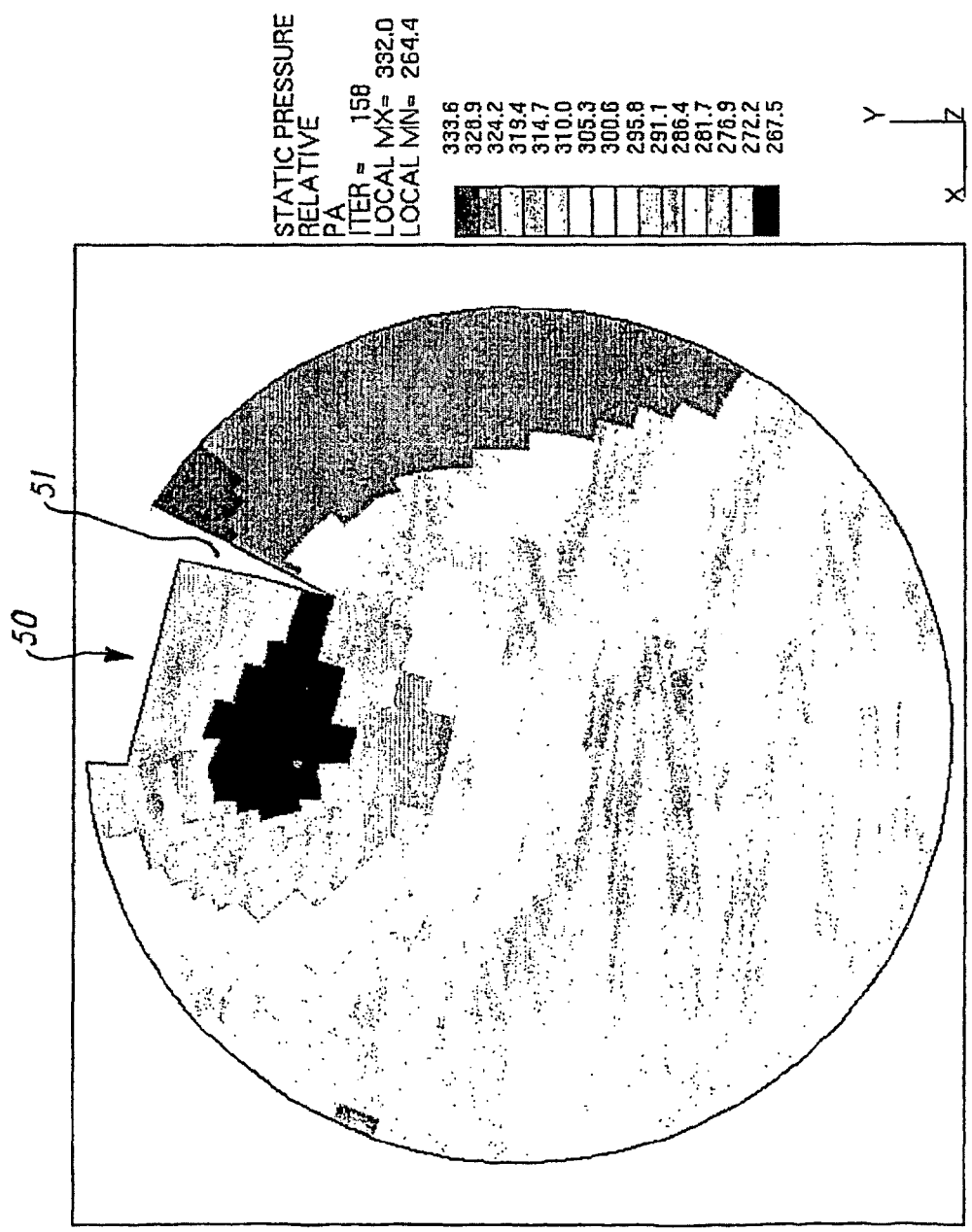
FIG. 10 shows a distribution of fluid pressures across the stent of FIG. 9 15 mm from the stent inlet.
Figure 11:
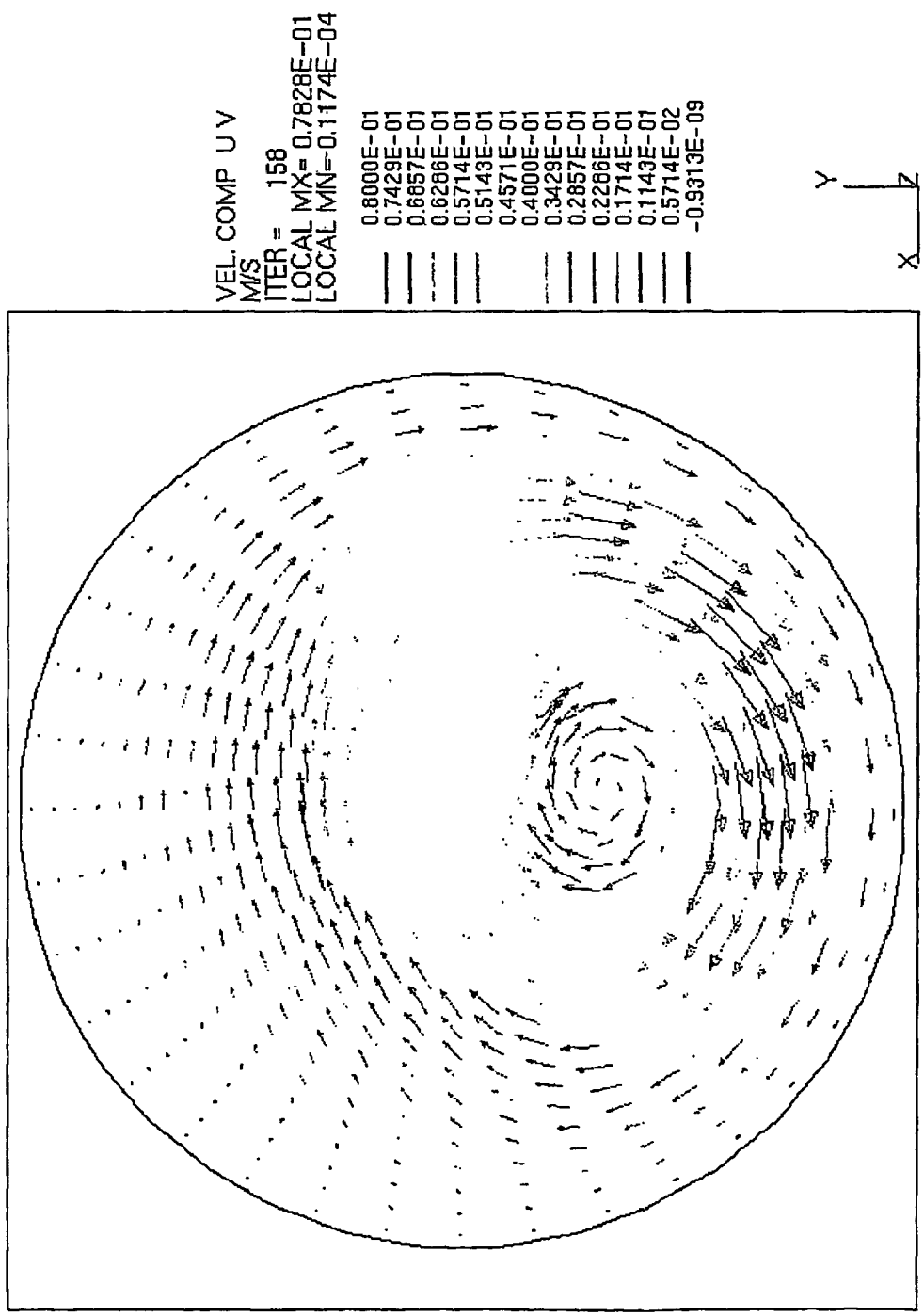
FIG. 11 shows a distribution of flow velocities across the stent of FIG. 9 50 mm downstream from the stent exit.
Figure 12:
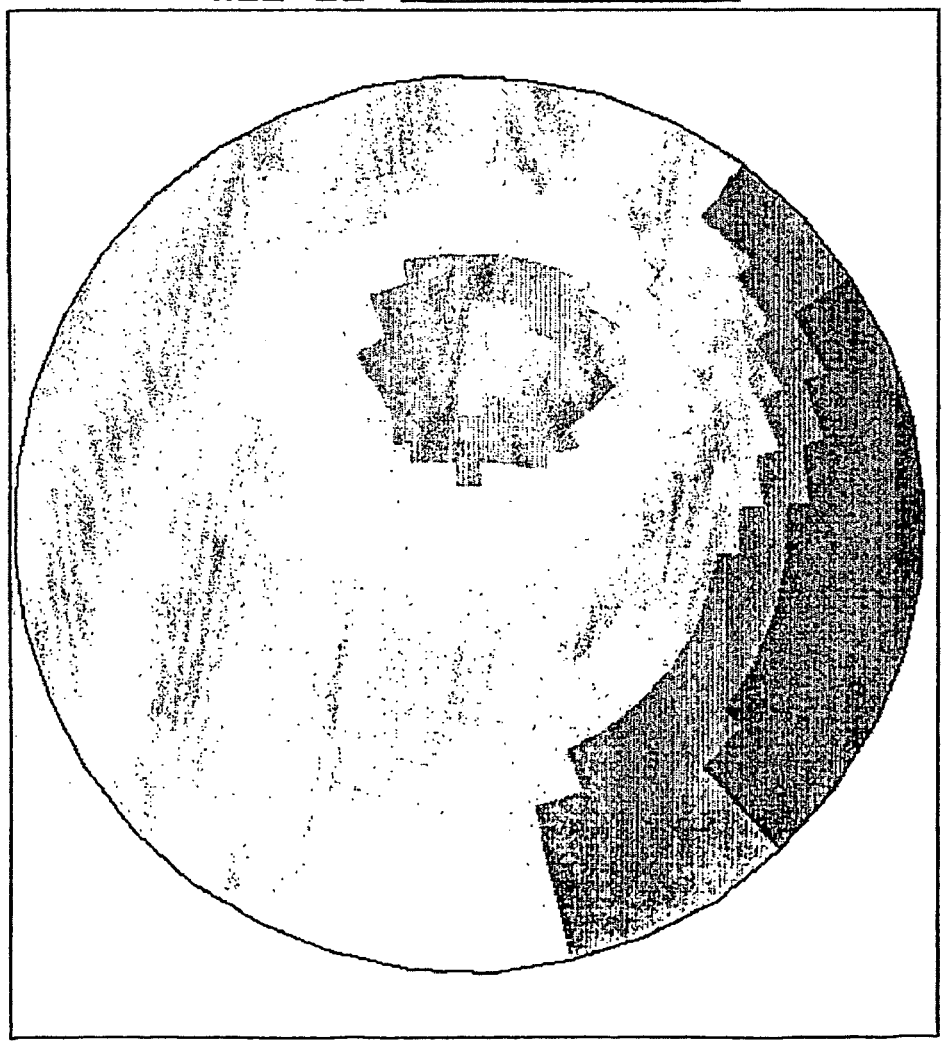
FIG. 12 shows a distribution of fluid pressures across the stent of FIG. 9 50 mm downstream from the stent exit.

In contrast, FIGS. 9 and 10 show the distribution of flow velocities and static pressures, respectively, 15 mm from the inlet of a stent also having a nominal length of 30 mm and diameter of 8 mm but with a helical formation 50 having a single side fin 51. As with the helical formation 2, the helical formation 50 defines a helix angle of 20°. FIGS. 11 and 12 show the distribution of flow velocities and static pressures, respectively, 50 mm downstream from the outlet of the stent having the helical formation 50. FIGS. 9 and 11 show that the helical formation generates spiral flow with more turbulence and dead spots than the helical formation 2. In addition, as can be seen from FIG. 12, the static pressure at the side walls of the tubing downstream from the stent is higher for the stent with the helical formation 50. This is undesirable as it increases the stress on the side walls of the blood vessels downstream of the stent.

Therefore, the invention has the advantage that the use of a helical formation having two fins, such as the helical formation 2, promotes better spiral flow patterns of fluid flowing through a conduit.

Although the example described above was in relation to helical formations in stents, helical formations using two fins could also be used in other applications to generate spiral flow of fluid within conduits. For example, the helical formation could be used in a graft for blood vessels, or in any other conduit where it is desired to generate spiral flow of fluid within the conduit.

The invention claimed is:

1. A conduit, comprising:
a body having a passage therethrough having an inner diameter;
an elongate member in the passage in engagement with the body, the elongate member defining at least a portion of a helix, the elongate member having a length and two side edges, defining a width;
a pair of fins extending inward from the elongate member and length-wise along the length of the elongate member, defining an intermediate portion of the elongate member between them, each of the fins having a base that is joined to one of the side edges and a free edge, the free edges defining an inner diameter that is smaller than the inner diameter of the passage to impart a spiral flow pattern onto fluid flowing through the passage, the elongate member having a helix angle such that over one revolution of the helix, a gap will exist between the side edges of the elongate member at the start of the revolution and the end of the revolution by more than the width of the elongate member.

2. The conduit according to claim 1, wherein each of the fins tapers in width from the base to the free edge.

3. The conduit according to claim 1, wherein the body is collapsible, and when collapsed, the fins fold toward each other over the intermediate portion of the elongate member, thereby placing the free edges closer to the intermediate portion than when not collapsed.

4. A blood flow implant conduit, comprising a helical formation, the helical formation being in the form of an insert that is inserted into at least a portion of the conduit, the helical formation comprising an elongate member defining at least a portion of a helix, the elongate member having a length and two side edges, defining a width and a generally U-shaped transverse cross-section, the elongate member comprising two inwardly extending portions, the inwardly extending portions being spaced from each other, extending lengthwise continuously along the length of the elongate member in a side-by-side relationship, and the inwardly extending portions extending inwardly along the length of the elongate member in side-by-side relationship, and the inwardly extending portions extending inwardly from the internal side walls of the conduit and defining an inner diameter that is smaller than an inner diameter of the conduit over the length of the insert, and the inwardly extending portions being configured to impart a spiral flow pattern onto fluid flowing in the conduit, the elongate member having a helix angle such that over one revolution of the helix, a gap will exist between the side edges of the elongate member at the start of the revolution and the end of the revolution by more than the width of the elongate member.

5. A helical formation according to claim 4, wherein the longitudinally extending member further comprises an intermediate portion that separates the two inwardly extending portions, the inwardly extending portions extending inwardly from the intermediate portion a greater amount than a width of the intermediate portion between the inwardly extending portions.

6. A helical formation according to claim 4, wherein the inwardly extending portions extend inwardly of the helix defined by the longitudinally extending member by substantially the same distance.

7. A helical formation according to claim 4, wherein the inwardly extending portions extend inwardly of the helix defined by the longitudinally extending member by different distances.

8. A helical formation according to claim 4, wherein the helical formation is for use in blood flow tubing for the human or animal body.

9. A helical formation according to claim 8, wherein the helical formation is for use in a graft.

10. A helical formation according to claim 8, wherein the helical formation is for use in a stent.

11. A helical formation according to claim 4, wherein the inwardly extending portions are movable to a collapsed position.

12. A helical formation according to claim 4, wherein each of the inward extending portions has a width that is less than the distance between the inward extending portions.

13. A helical formation according to claim 4, wherein each of the inward extending portions joins one of the side edges and has a width that gradually reduces in an inward direction.

* * * * *

UNITED STATES PATENT AND TRADEMARK OFFICE
CERTIFICATE OF CORRECTION

PATENT NO.         : 7,185,677 B2
APPLICATION NO. : 10/496212
DATED              : March 6, 2007
INVENTOR(S)        : John Graeme Houston et al.

Page 1 of 1

It is certified that error appears in the above-identified patent and that said Letters Patent is hereby corrected as shown below:

In the Claims:

Column 4, lines 40, 41 and 42, delete "and the inwardly extending portions extending inwardly along the length of the elongate member in side-by-side relationship,"

Signed and Sealed this

Twenty-third Day of October, 2007

JON W. DUDAS
*Director of the United States Patent and Trademark Office*